(12) United States Patent
Denholm et al.

(10) Patent No.: US 6,979,563 B1
(45) Date of Patent: Dec. 27, 2005

(54) ATTENUATION OF TUMOR GROWTH, METASTASIS AND ANGIOGENESIS

(75) Inventors: Elizabeth M. Denholm, Pointe Claire (CA); Yong-Qing Lin, Nanuet, NY (US); Paul J. Silver, Spring City, PA (US)

(73) Assignee: BioMarin Enzymes, Inc., Novato, CA (US)

( * ) Notice: Subject to any disclaimer, the term of this patent is extended or adjusted under 35 U.S.C. 154(b) by 425 days.

(21) Appl. No.: 09/715,965

(22) Filed: Nov. 17, 2000

Related U.S. Application Data

(60) Provisional application No. 60/165,957, filed on Nov. 17, 1999.

(51) Int. Cl.$^7$ ............................................. C12N 9/00
(52) U.S. Cl. ................................................ 435/183
(58) Field of Search ....................... 435/232; 424/94.5, 424/457, 468

(56) References Cited

U.S. PATENT DOCUMENTS

| | | | |
|---|---|---|---|
| 4,696,816 A | * | 9/1987 | Brown ........................ 424/94 |
| 5,567,417 A | | 10/1996 | Sasisekharan et al. | |
| 5,945,403 A | | 8/1999 | Folkman et al. | |

FOREIGN PATENT DOCUMENTS

| | | | |
|---|---|---|---|
| JP | 51075042 | * | 6/1979 |
| WO | WO 96/01648 | | 1/1996 |
| WO | WO 96/01894 | | 1/1996 |
| WO | WO 96/08559 | | 3/1996 |

OTHER PUBLICATIONS

Takeuchi, Brit. J. Cancer, 1972, 26(2), 115-119.*
Crum, et al., "A new class of steroids inhibits angiogenesis in the presence of heparin or a heparin fragment," *Science* 230(4732): 1375-1378 (1985).
Culp, et al., "Two functionally distinct pools of glycosaminoglycan in the substrate adhesion site of murine cells," *J. Cell Biol.* 79(3):788-801 (1978).
Denholm, et al., "The effects of bleomycin on alveolar macrophage growth factor secretion," *Am J Pathol.* 134(2): 355-63 (1989).
Denholm, et al., "Chondroitinase AC inhibits tumor cells invasion, proliferation, and angiogenesis," *FASEB J* 14(4): A702 (2000).
Denholm, et al., "Anti-tumor activities of chondroitinase AC and chondroitinase B: inhibition of angiogenesis, proliferation and invasion," *Eur J Pharmacol* 416(3): 213-221 (20001).
Faassen, et al., "A cell surface chondroitin sulfate proteoglycan, immunologically related to CD44, is involved in type I collagen-mediated melanoma cell motility and invasion," *J. Cell Biol.* 116(2):521-531 (1992).

Faassen, et al., "Cell surface CD44-related chondroitin sulfate proteoglycan in required for transforming growth factor-beta-stimulated mouse melanoma cell motility and invasive behavior on type I collagen," *J. Cell Science* 105(Pt 2):501-511 (1993).
Folkman, "Angiogenesis in cancer, vascular, rheumatoid and other disease," *Nat Med* 1(1):27-31 (1995).
Folkman, "Successful treatment of an angiogenic disease," *N. Engl. J. Med.* 320(18): 1211-1212 (1989).
Folkman, "Tumor angiogenesis: therapeutic implications," *N. Engl. J. Med.* 285(21): 1182-1186 (1971).
Folkman, et al., "Angiogenesis inhibition and tumor regression caused by heparin or a heparin fragment in the presence of cortisone," *Science* 221(4612): 719-725 (1983).
Folkman, et al., "Control of angiogenesis with synthetic heparin substitutes," *Science* 243(4897): 1490-1493 (1989).
Forrester, et al., "A paradigm for restenosis based on cell biology: clues for the development of new preventive therapies," *J. Am. Coll. Cardiol.* 17(3):758-769 (1991).
Gu, et. al., "Purification, characterization and specificity of chondroitin lyases and glycuronidase from *Falvobacterium heparinum*," *Biochem. J.* 312(Pt 2):569-577 (1995).
Henke, et. al., "CD44-related chondroitin sulfate proteoglycan, a cell surface receptor implicated with tumor cell invasion, mediates endothelial cell migration on fibrinogen and invasion into a fibrin matrix," *J. Clin. Invest.* 97(11):2541-2552 (1996).
Ingber, et al., "Inhibition of angiogenesis through modulation of collagen metabolism," *J. Lab. Invest.* 59: 44-51 (1989).
Ingber, et al., "A possible mechanism for inhibition of angiogenesis by angiostatic steroids: induction of capillary basement membrane dissolution," *Endocrinol.* 119(4): 1768-1775 (1986).
Ingber, et al., "Mechanochemical switching between growth and differentiation during fibroblast growth factor-stimulated angiogenesis in vitro: role of extracellular matrix," J. Cell. Biol. 109(1): 317-330 (1989).

(Continued)

*Primary Examiner*—Michael Meller
(74) *Attorney, Agent, or Firm*—Pabst Patent Group LLP

(57) ABSTRACT

A highly purified and specific glycosaminoglycan degrading enzyme, chondroitinase AC, and to a lesser extent, chondroitinase B, can be used in the treatment of metastatic cancers and in other disorders characterized by angiogenesis. The enzymatic removal of chondroitin sulfates A and C, and to a lesser extent, chondroitin sulfate B, from cell surfaces directly decreases the ability of tumor cells to invade blood vessels and thus prevents the formation of metastatic, or secondary tumors; inhibits tumor cell growth; and decreases angiogenesis by inhibiting both endothelial cell proliferation and capillary formation. Decreasing the formation of new blood vessels into the tumor in turn decreases the potential for tumor growth, and further decreases the ability of tumor cells to invade the bloodstream. These effects are opposite to the prometastatic effects of tumor-secreted heparanase.

20 Claims, 5 Drawing Sheets

OTHER PUBLICATIONS

Jackson et. al., "Glycosaminoglycans: molecular properties, protein interactions, and role in physiological processes," *Physiol. Rev.* 71(2):481-530 (1991).

Jin-Inchi, et al., "Inhibition of experimental metastasis of murine Lewis lung carinoma by an inhibitor of glucosylceramide synthase and its possible mechanism of action," *Cancer Res.* 50:6731-6737 (1990).

Lida, et al., "Cell surface chondroitin sulfate proteoglycans in tumor cell adhesion, motility and invasion," *Sem. Cancer Biol.* 7:155-162, (1996).

Linhardt, et al., "Polysaccharide lyases," *Appl. Biochem. Biotech.* 12(2): 135-176 (1986).

Linn et. al., "Isolation and characterization of two chondroitin lyases from Bacteroides thetaiotaomicron," *J. Bacteriol.* 156(2):859-866 (1983).

Meyer, et al., "Mechanisms of tumour metastasis," *Eur. J. Cancer* 34(2):214-221 (1998).

Michelacci, et al., "Isolation and characterization of an induced chondroitinase ABC from *Flavobacterium heparinum*," *Biochim. Biophys. Acta.* 923(2):291-301 (1987).

Murray, et al., "Purification and partial amino acid sequence of a bovine cartilage-derived collagenase inhibitor," *J. Biol. Chem.* 261(9): 4154-4159 (1986).

Nakajima, et al., "Heparan sulfate degradation: relation to tumor invasive and metastatic properties of mouse B16 melanoma sublines," *Science* 220(4597):611-613 (1983).

Richardson, et al., "Transient morphological and biochemical alterations of arterial proteoglycan during early wound healing," *Exp. Mol. Pathol.* 58(2):77-95 (1993).

Sato, et al., "Submit structure of Chondroitinase ABC from *Proteus vulgaris*," *Agric. Biol. Chem.* 50:1057-1059 (1986).

Tabas, et al., "Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation," *J. Biol. Chem.* 268(27):20419-20432 (1993).

Takeuchi, "Effect of chondroitinases on the growth of solid Ehrlich ascites tumour," *Brit J Cancer* 26(2): 115-119 (1972).

Trochan, et al., "Evidence of involvement of CD44 in endothelial cell proliferation, migration and angiogenesis in vitro," *Int. J. Cancer* 66:664-668 (1996).

Volpi, "Fast moving and slow moving heparins, dermatan sulfate, and chondroitin sulfate: qualitative and quantitative analysis by agarose-gel electrophoresis," *Carbohydrate Res.* 247:263-278 (1993).

Yeo, et al., "Alterations in proteoglycan synthesis common to healing wounds and tumors," Am. J. Pathol. 138(6):1437-1450 (1991).

Zawadzki, et al., "Blackade of metastasis formation by CD44-receptor globulin," *Int. J. Cancer* 75(6):919-924 (1998).

* cited by examiner

ATTENUATION OF TUMOR GROWTH, METASTASIS AND ANGIOGENESIS

This claims priority to U.S. Ser. No. 60/165,957 filed Nov. 17, 1999, entitled "Attenuation of Tumor Growth, Metastasis and Angiogenesis" by Elizabeth M. Denholm, Yong-Qing Lin, and Paul J. Silver.

BACKGROUND OF THE INVENTION

The present invention is a method and formulations using chondroitinase AC and chondroitinase B, glycosaminoglycan degrading enzymes, to inhibit tumor cell growth, metastasis and angiogenesis, and thereby to treat or prevent certain cancers.

Proteoglycans on the cell surface and in the extracellular matrix contain variable glycosaminoglycan chains, which include heparan sulfate and chondroitin sulfates A, B, or C. While some proteoglycans contain only one type of glycosaminoglycan, others contain a mixture of heparan and chondroitin sulfates (Jackson et. al., *Physiol. Rev.* 71:481–530, 1991). Extracellular proteoglycans form a structural framework for cells and tissues, and together with cell-associated proteoglycans, have major functions in regulating cell adhesion, migration, and proliferation. Disruption of the normal synthesis and function of proteoglycans is thought to have an important role in tumor cell metastasis.

Tumor metastasis is the process by which malignant cells from a tumor spread throughout the body and develop into multiple secondary tumors (Lida et. al. *Sem. Cancer Biol.* 7:155–162, 1996; Meyer and Hart *Eur. J. Cancer* 34:214–221, 1998). In order to spread to other parts of the body, tumor cells must escape from the primary or original tumor, enter the blood stream or lymphatic system, and from there invade the tissue of other organs, where they multiply and form new tumors. Escape from the primary tumor and invasion into other organs is a complex multi-step process. Metastasis involves changes in tumor cell adhesion and motility, secretion of proteolytic enzymes, chemoattractants, and proteoglycans. In addition to these tumor cell activities, angiogenesis, or the formation of new blood vessels, is also a vital step in the metastatic process (Folkman *Nature Medicine* 1:27–31, 1995).

The involvement of different types of glycosaminoglycans in tumor cell metastasis has been investigated. Heparan sulfates on the cell surface appear to inhibit cell motility (Culp et. al. *J. Cell Biol.* 79:788–801, 1978). Heparan sulfates in the extracellular matrix act to impede cell movement through the formation of a tight network with other matrix components. Tumor cells can secrete a glycosaminoglycan-degrading enzyme, heparanase, which cleaves heparan sulfates and enhances escape from the tumor and promotes metastasis (Culp, et al. *J. Cell Biol.* 79:788–801, 1978; Nakajima et. al. *Science* 220:611–613, 198).

In contrast, chondroitin sulfates have never been linked to an enhancement of motility of both endothelial and tumor cells (Culp et. al. 1978). When formation of chondroitin sulfate proteoglycans is inhibited by treating cells with -xylosides, motility, migration and the ability to invade matrix material are inhibited (Henke et. al., *J. Clin. Invest.* 97:2541–2552, 1996; Faassen et. al., *J. Cell Biol.* 116: 521–531, 1992 and Trochan et. al. *Int. J. Cancer* 66:664–668, 1996). Removal of chondroitin sulfates from the cell surface with chondroitinase ABC also decreases cell motility (Faassen et. al., 1992); however the effects of this enzyme on invasion or metastasis, or on angiogenesis are not known.

It is an object of the present invention to provide methods for treating or preventing tumor growth, metastasis or angiogenesis.

It is a further object of the present invention to provide formulations for treating or preventing tumor growth, metastasis or angiogenesis.

SUMMARY OF THE INVENTION

A highly purified and specific glycosaminoglycan degrading enzyme, chondroitinase AC, and to a lesser extent, chondroitinase B, can be used in the treatment of metastatic cancers. The enzymatic removal of chondroitin sulfates A and C, and to a lesser extent, chondroitin sulfate B, from tumor cell surfaces effectively A) decreases their ability to proliferate when stimulated by oncogenic growth factors, B) decreases the ability of tumor cells to invade blood vessels and thus prevents the formation of metastatic, or secondary tumors, and C) decreases angiogenesis by inhibiting both endothelial cell proliferation and capillary formation. Decreasing the formation of new blood vessels into the tumor in turn decreases the potential for tumor growth, and further decreases the ability of tumor cells to invade the bloodstream. These anti-metastatic effects of chondroitinases are opposite to the pro-metastatic effects of tumor secreted-heparanases.

BRIEF DESCRIPTION OF THE DRAWINGS

FIG. 1A is the release of $^{35}$S-glycosaminoglycans after treatment with the indicated concentration (control., 0.1, 1 and 2 IU/ml) of enzyme for one hr. FIG. 1B is the release of $^{35}$S-glycosaminoglycans after treatment with 1.0 IU/ml of enzyme for the indicated time, zero, 5, 15 30 and 60 minutes. Data are the cpm/well of $^{35}$S-glycosaminoglycans released by enzyme treatment or by medium along (control), mean±sem of representative experiments performed in quadruplicate.

DETAILED DESCRIPTION OF THE INVENTION

Figure 1A:
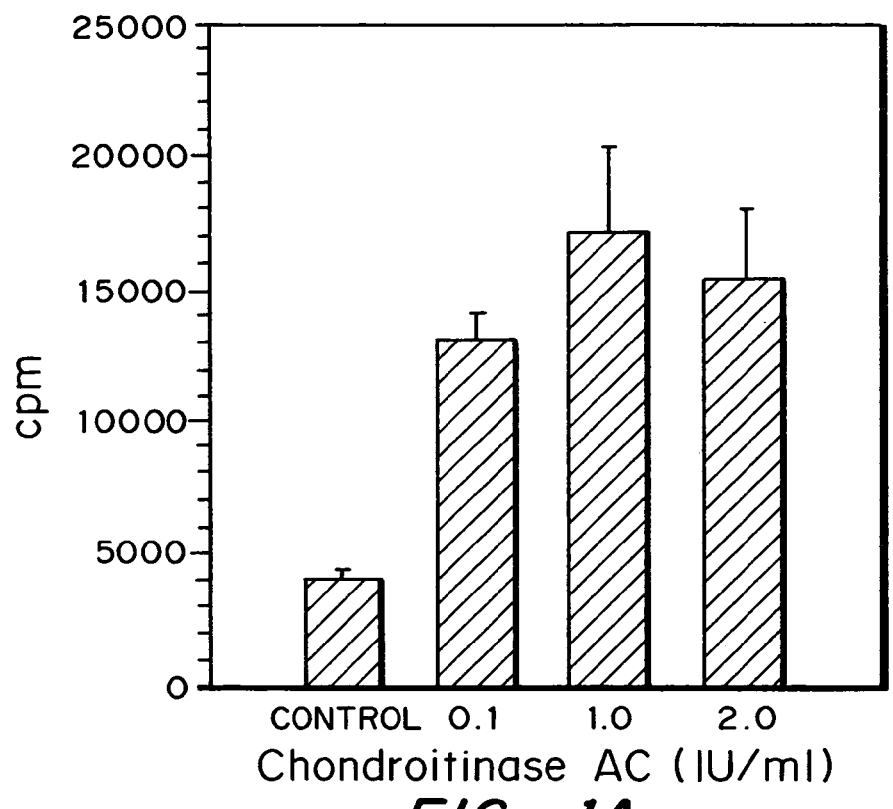
FIGS. 1A and 1B are graphs of the release of sulfated glycosaminoglycans from human SK-MEL melanoma cells, following treatment with *Flavobacterium heparinum* derived Chondroitinase AC.

Events in the metastasis of, growth of, and angiogenesis within cancerous tumors can be inhibited by the use of one or more highly purified glycosaminoglycan degrading enzymes derived from various sources, but most preferably from *Flavobacterium heparinum*. Glycosaminoglycans, including chondroitin sulfates A, B or C, and heparan sulfate, are the sulfated polysaccharide components of proteoglycans located on cell surfaces, where they act as co-receptors in interactions between cell determinant proteins and extracellular matrix components such as hyaluronic acid and collagens; and in the extracellular space where they form the structure of the extracellular matrix and serve as a supporting and organizational structure of tissues and organs.

Chondroitin sulfates have been found to be associated with a cell adhesion molecule, CD44, which is important in tumor cell invasion. The biological activities of CD44 have been linked to the chondroitin sulfates on this protein (Faassen, et. al. *J. Cell Science* 105:501–511, 1993). Antibodies to CD44 inhibit formation of metastatic tumors in vivo (Zawadzki et. al. Int. *J. Cancer* 75:919–924, 1998), and inhibit endothelial cell migration and formation of capillary like structures in vitro (Henke et. al. 1996 and Trochan et. al. 1996).

The combination of data from studies on the effects of inhibiting chondroitin sulfates and from studies on the effects of anti-CD44 antibodies, all lead to the conclusion that chondroitin sulfates play a vital role in both tumor cell as well as endothelial cell growth and vessel formation (angiogenesis). This role for chondroitin sulfates in angiogenesis is relevant to its role in both sustained growth of tumors and tumor metastasis, since formation of new blood vessels is vital in supplying nutrients to a growing tumor and in providing a pathway by which invasive tumor cells travel to distant organs and form secondary tumors.

The Chondroitinase AC and chondroitinase B described in the examples are glycosaminoglycan degrading enzymes from *Flavobacterium heparinum*. These enzymes remove and degrade glycosaminoglycans from proteoglycans, and thereby modulate the interactions involved in tumor cell invasion and proliferation, as well as the processes involved in endothelial capillary formation and proliferation. Chondroitinase AC and chondroitinase B regulate tumor cell growth and metastasis by: i) cleaving chondroitin sulfate proteoglycans from cell surfaces; ii) reducing the invasive capacity of tumor cells by degrading chondroitin sulfate GAGs linked to CD44; iii) decreasing endothelial cell proliferation and capillary formation and thereby reducing the supply of nutrients to the tumor and reducing tumor cell access to the bloodstream; and iv) directly inhibiting growth factor-dependent proliferation of tumors.

Enzyme Formulations

Enzymes

Glycosaminoglycans are unbranched polysaccharides consisting of alternating hexosamine and hexuronic residues which carry sulfate groups in different positions. This class of molecules can be divided into three families according to the composition of the disaccharide backbone. These are: heparin/heparan sulfate [HexA-GlcNAc(SO4)]; chondroitin sulfate [HexA-GalNAc]; and keratan sulfate [Gal-GlcNAc].

Representative glycosaminoglycan degrading enzymes include heparinase 1 from *Flavobacterium heparinum*, heparinase 2 from *Flavobacterium heparinum*, heparinase 3 from *Flavobacterium heparinum*, chondroitinase AC from *Flavobacterium heparinum*, and chondroitinase B from *Flavobacterium heparinum*, heparinase from *Bacteroides* strains, heparinase from *Flavobacterium* Hp206, heparinase from *Cytophagia* species, chondroitin sulfate degrading enzymes from *Bacteroides* species, chondroitin sulfate degrading enzymes from *Proteus vulgaris*, chondroitin sulfate degrading enzymes from *Microcossus*, chondroitin sulfate degrading enzymes from *Vibrio* species, chondroitin sulfate degrading enzymes from *Arthrobacter aurescens*, these enzymes expressed from recombinant nucleotide sequences in bacteria and combinations thereof. Other enzymes which degrade glycosaminoglycans are present in mammalian cells and include heparanases, arylsulfatase B, N-acetylgalactosamine-6-sulfatase, and iduronate sulfatase.

The chondroitin sulfate family includes seven sub-types designated unsulfated chondroitin sulfate, oversulfated chondroitin sulfate and chondroitin sulfates A–E which vary in the number and position of their sulfate functional groups. Additionally, chondroitin sulfate B, also referred to as dermatan sulfate, differs in that iduronic acid is the predominant residue in the alternative hexuronic acid position.

Chondroitin sulfates A, B and C are the predominant forms found in mammals and may be involved in the modulation of various biological activities including cell differentiation, adhesion, enzymatic pathways and hormone interactions. The presence of chondroitin sulfate proteoglycans is elevated in the later stages of cell growth in response to tissue and vessel damage, as reported by Yeo, et al., *Am. J. Pathol.* 138:1437–1450, 1991, Richardson and Hatton, *Exp. Mol. Pathol.* 58:77–95, 1993 and Forrester, et al., *J. Am. Coll. Cardiol.* 17:758–769, 1991. Chondroitin sulfates also have been associated with events involved in the progression of vascular disease and lipoprotein uptake as described by Tabas, et al., *J. Biol. Chem.*, 268(27):20419–20432, 1993.

Chondroitinases have been isolated from several bacterial species: *Flavobacterium heparinum, Aeromonas* sp., *Proteus vulgaris, Aurebacterium* sp. and *Bacillus thetaiotamicron* (Linhardt et. al., 1986; Linn et. al., J. *Bacteriol.* 156:859–866, 1983; Michelacci et. al., *Biochim. Biophys. Acta.* 923:291–201, 1987; and Sato et. al., *Agric. Biol. Chem.* 50:1057–1059, 1986). PCT/US95/08560 "Chondroitin Lyase Enzymes" by Ibex Technologies R and D, Inc., et al. describes methods for purification of naturally produced chondroitinases, especially separation of chondroitinase AC from chondroitinase B, as well as expression and purification of recombinant chondroitinases. Mammalian enzymes which degrade chondroitin sulfates include arylsulfatase B, N-acetylgalactosamine-6-sulfatase, and iduronate sulfatase.

Formulations

Pharmaceutical compositions are prepared using the glycosaminoglycan degrading enzyme as the active agent to inhibit tumor growth or angiogenesis based on the specific application. Application is either topical, localized, or systemic. Any of these formulations may also include preservatives, antioxidants, antibiotics, immunosuppressants, and other biologically or pharmaceutically effective agents which do not exert a detrimental effect on the glycosaminoglycan degrading enzyme or cells. For treatment of tumors, the composition may include a cytotoxic agent which selectively kills the faster replicating tumor cells, many of which are known and clinically in use.

For topical application, the glycosaminoglycan degrading enzyme is combined with a carrier so that an effective dosage is delivered, based on the desired activity, at the site of application. The topical composition can be applied to the skin for treatment of diseases such as psoriasis. The carrier may be in the form of an ointment, cream, gel, paste, foam, aerosol, suppository, pad or gelled stick. A topical composition for treatment of eye disorders consists of an effective amount of glycosaminoglycan degrading enzyme in a ophthalmically acceptable excipient such as buffered saline, mineral oil, vegetable oils such as corn or arachis oil, petroleum jelly, Miglyol 182, alcohol solutions, or liposomes or liposome-like products.

Compositions for local or systemic administration, for example, into a tumor, will generally include an inert diluent. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

For directed internal topical applications, for example for treatment of solid tumors, resection sites, or hemorrhoids, the composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The glycosaminoglycan degrading enzyme can also be administered in combination with a biocompatible polymeric implant which releases the glycosaminoglycan degrading enzyme over a controlled period of time at a selected site. Examples of preferred biodegradable polymeric materials include polyanhydrides, polyorthoesters, polyglycolic acid, polyesters such as polylactic acid, polyglycolic acid, polyethylene vinyl acetate, and copolymers and blends thereof. Examples of preferred non-biodegradable polymeric materials include ethylene vinyl acetate copolymers.

Other Therapeutic Agents which can be Administered in Combination

The glycosaminoglycan degrading enzymes can be administered alone or in combination with other treatments. For example, the enzymes can be administered with antibiotics, cytokines, and anti-inflammatories such as cortisone, and/or other types of angiogenic inhibitors. Other combinations will be apparent to those skilled in the art. In some embodiments, the enzymes are administered with a barrier, such as methylcellulose or other polymeric material, either topically at the time of surgery or incorporated into the barrier, which is inserted at the time of surgery.

Methods of Treatment

Disorders

A variety of disorders to be treated. In the principal embodiment, the glycosaminoglycan degrading enzymes chondroitinase AC and chondroitinase B are used to inhibit formation, growth and/or metastasis of tumors, especially solid tumors. Examples of tumors including carcinomas, adenocarcinomas, lympohomas, sarcomas, and other solid tumors, as described in U.S. Pat. No. 5,945,403 to Folkman, et al., solid tumors; blood born tumors such as leukemias; tumor metastasis; benign tumors, for example hemangiomas, acoustic neuromas, neurofibromas, trachomas, and pyogenic granulomas. Other disorders involving angiogenesis including rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, atherosclerosis, scleroderma, and hypertrophic scars, i.e., keloids, and diseases that have angiogenesis as a pathologic consequence such as cat scratch disease (*Rochele minalia quintosa*) and ulcers (*Helicobacter pylori*), can also be treated. Angiogenic inhibitors can be used to prevent or inhibit adhesions, especially intra-peritoneal or pelvic adhesions such as those resulting after open or laproscopic surgery, and burn contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophyy, as well as obesity, may also be treated by inhibition of angiogenesis. These disorders may involve increases in size or growth of other types of normal tissue, such as uterine fibroids, prostatic hypertrophy, and amyloidosis.

Angiogenesis, the proliferation and migration of endothelial cells that result in the formation of new blood vessels, is an essential event in a wide variety of normal and pathological processes. For example, angiogenesis plays a critical role in embryogenesis, wound healing, psoriasis, diabetic retinopathy, and tumor formation, as reported by Folkman, J. Angiogenesis and its inhibitors. In: V. T. DeVita, S. Hellman and S. A. Rosenberg (eds.). *Important Advances in Oncology*, pp. 42–62, (J. B. Lippincott Co., Philadelphia, 1985); Brem, H., et al., *Brain tumor angiogenesis*. In: P. L. Komblith and M. D. Walker (eds.), *Advances in Neuro-Oncology*, pp. 89–101. (Future Publishing Co., Mount Kisco, N.Y. 1988); Folkman, J. Tumor angiogenesis: therapeutic implications. *N. Engl. J. Med.*, 285; 1182–1186 (1971); and Folkman, J. Successful treatment of an angiogenic disease. *N. Engl. J. Med.*, 320: 1211–1212 (1989).

Identification of several agents that inhibit tumor angiogenesis has provided a conceptual framework for the understanding of angiogenesis in general. The inhibition of angiogenesis by certain steroids and heparin derivatives, reported by Folkman, J., et al., *Science* 221: 719 (1983); and Murray, J. B., et al., *J. Biol. Chem.*, 261: 4154–4159 (1986); led to studies elucidating the crucial role of remodeling of the extracellular matrix in angiogenesis. These agents apparently prevent angiogenesis by specifically disrupting the deposition and cross-linking of collagen, as reported by Ingber, D., and Folkman, *J. Lab. Invest.*, 59: 44–51 (1989).

Other studies on inhibition of angiogenesis have highlighted the importance of enzyme mediated remodeling of the extracellular matrix in capillary growth and proliferation (Folkman, J., et al., *Science* 221: 719–725 (1983); Ingber, D., et al. *Lab. Invest.* 59: 44–51 (1989); Folkman, J., et al., *Science* 243: 1490–1493 (1989); Krum, R., et al., *Science* 230: 1375–1378 (1985); Ingber, D., et al., *Endocrinol.* 119: 1768–1775 (1986); and Ingber, D., et al., *J. Cell. Biol.* 109: 317–330 (1989)).

Methods of Administration

The composition can be administered systemically using any of several routes, including intravenous, intra-cranial, subcutaneous, orally, or by means of a depot. The composition can be administered by means of an infusion pump, for example, of the type used for delivering insulin or chemotherapy to specific organs or tumors, or by injection.

Chondroitinase AC and chondroitinase B can be injected using a syringe or catheter directly into a tumor or at the site of a primary tumor prior to or after excision; or systemically following excision of the primary tumor.

The enzyme formulations are administered topically or locally as needed. For prolonged local administration, the enzymes may be administered in a controlled release implant injected at the site of a tumor. For topical treatment of a skin condition, the enzyme formulation may be administered to the skin in an ointment or gel.

Effective Dosage

An effective dosage can be determined by the amount of enzyme activity units (IU) per tumor. An expected effective dosage range includes 0.1 to 250 IU/tumor for expected tumor sizes ranging from 20 $mm^3$ to 15 $cm^3$.

The present invention will be further understood by reference to the following non-limiting examples.

EXAMPLE 1

Enzyme Substrate Specificity

Chondroitinase B (no EC number) and chondroitinase AC (EC 4.2.2.5) are native enzymes of *Flavobacterium heparinum* and can also be recombinantly expressed in this same bacterium (Gu et. al., *Biochem. J.* 312:569–577 (1995)). Specific activity and substrate specificity were determined for each enzyme, using a kinetic spectrophotometric assay, performed essentially as described by Gu et al. (1995). In these assays, enzyme concentrations were 0.25 IU/ml and substrate concentrations were 0.5 mg/ml (chondroitin sulfate B and chondroitin sulfate AC) or 0.75 mg/ml (heparan sulfate). The specific activities of the enzymes were: 97 IU/mg for Chondroitinase B and 221 IU/mg for chondroitinase AC.

The substrate specificity of ultra-purified Chondroitinase B and AC were determined by testing the ability of the enzymes to degrade chondroitin sulfate B, chondroitin sulfate A, chondroitin sulfate C, and heparan sulfate. As shown in Table 1, both enzymes were active towards the corresponding sulfated glycosaminoglycan, with 0.2% or less activity against any of the other glycosaminoglycans. These results confirm the substrate specificity of the purified Chondroitinase B and Chondroitinase AC used in this application.

TABLE 1

Comparative Enzymatic Activities Against Glycosaminoglycans

| Enzyme | Substrate | | | |
|---|---|---|---|---|
| | CSB | CSA | CSC | HS |
| Chondroitinase B | | | | |
| IU/ml | 399 | 0.04 | 0.03 | 0.92 |
| (relative activity) | (100) | (0.01) | (0.01) | (0.230 |
| Chondroitinase AC | | | | |
| IU/ml | 0.604 | 1238 | 735 | 2.2 |
| (relative activity) | (0.05) | (100) | (59) | (0.18) |

Enzyme activities are shown as IU/ml with each substrate, and as the relative activity towards each substrate. Relative activity was determined after assigning 100% for the preferred substrate (CSB for chondroitinase B, CSA for chondroitinase AC. CSB=chondroitin sulfate B; CSA=chondroitin sulfate A; CSC=chondroitin sulfate C; HS=heparan sulfate). Substrate concentrations were 500 mg/ml (CSB, CSA, CSC) or 750 g/ml (HS).

EXAMPLE 2

Removal of Glycosaminoglycans from Cells

The effectiveness of the chondroitinase AC in removing sulfated glycosaminoglycans from cells was examined using cells with glycosaminoglycans labeled by incubation with $Na^{35}SO_4$ (Dupont, NEN). Human melanoma cells (SK-MEL) were plated at a density of $6 \times 10^4$ cells/well in 24 well plates, in MEM with 10% serum and 25 mCi/ml of $Na_2^{35}SO_4$, and incubation continued for 2.5 days. The medium was removed and cells rinsed 2× with MEM then treated with Chondroitinase AC as indicated. Medium was removed and radioactivity determined. The release of sulfated glycosaminoglycans from cells by enzyme was expressed as cpm/well.

Figure 1B:
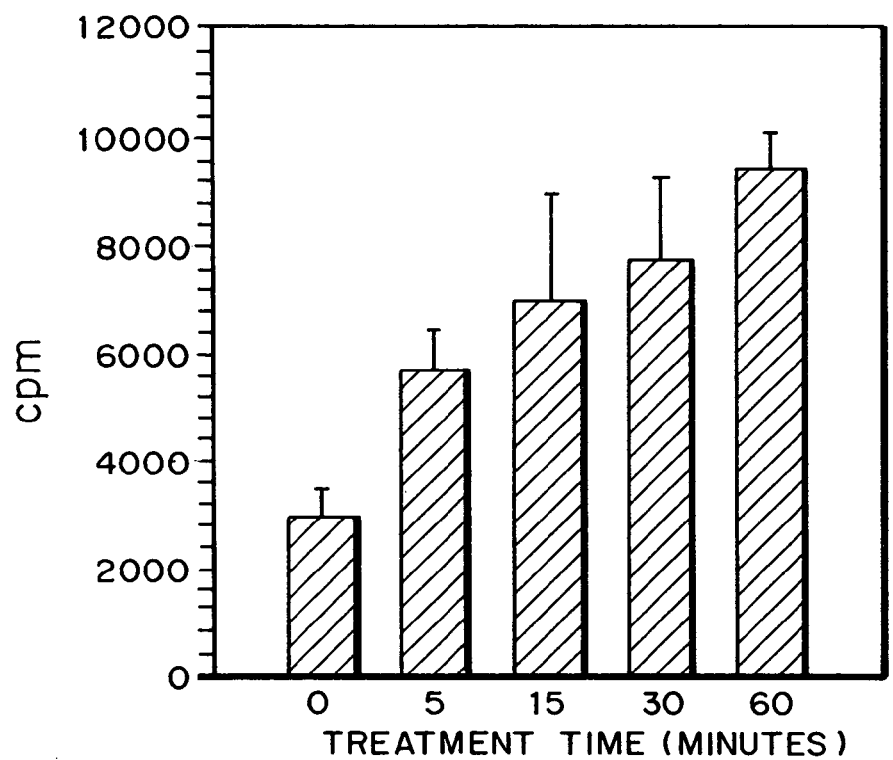

Cells were exposed to 0.1, 1.0 or 2.0 IU/ml of Chondroitinase AC, at 37 C. for 1 hour. As shown in FIG. 1A, maximal release of sulfated GAGs by chondroitinase AC was achieved with 1.0 IU/ml of enzyme. Further experiments were done in which SK cells were treated with 1.0 IU/ml of chondroitinase AC for 5 to 60 minutes. FIG. 1B illustrates that the release of sulfated glycosaminoglycans from SK cells was also dependent on the length of time that they were exposed to chondroitinase AC.

Other experiments were done to identify the radiolabelled glycosaminoglycans released into the medium after chondroitinase AC treatment of cells. Cells were treated with 1.0 IU/ml of chondroitinase AC for 1 hour at 37° C., after which glycosaminoglycans in the medium were precipitated with Cetavalon (Aldrich Chemicals, St. Louis, Mo.) and analyzed with agarose gel electrophoresis (Volpi, Carbohydrate Res. 247:263–278, 1993). The $^{35}$S-glycosaminoglycans released in to the medium were identified as disaccharide fragments of chondroitin sulfate based on the distance migrated into the agarose gels. As measured from the wells, migration distances into the gels for glycosaminoglycan standards were: 25 mm for heparan sulfate, 31 mm for dermatan sulfate, 37 mm for chondroitin sulfate, and 10 mm for fragments of chondroitin sulfate prepared by digestion with chondroitinase AC. The $^{35}$S-glycosaminoglycans released from cells migrated 10 mm into the gels.

EXAMPLE 3

Effects on Tumor Cell Invasion

The effects of Chondroitinase AC on tumor cell invasion were assessed in an in vitro assay. Two human cell lines were used: SK-MEL-2, a melanoma and HT-1080, a fibrosarcoma, both obtained from the ATCC in Manassas, Va. Each cell line was grown to a density of approximately 4×10$^5$ cells/well, in MEM with 10% serum. Cells were rinsed with PBS, then treated with the indicated concentration of Chondroitinase AC in serum free medium for one hour at 37 C. Following enzyme treatment, cells were rinsed with serum free medium, removed from dishes by trypsinization and resuspended in medium containing 1% serum containing the indicated concentration of chondroitinase AC.

The invasion assay was performed in 8 mm pore polycarbonate filter cell culture inserts (Falcon, Franklin Lakes, N.J.). Insert filters were pre-coated with 25 μg of Matrigel (Collaborative Biochemicals, Cambridge, Mass.) in serum free medium. Coated filters were dried overnight and equilibrated with serum free medium for 1 hr prior to use. Fifty thousand tumor cells in medium with 1% BSA were placed on top of the filters, and fibroblast conditioned medium (prepared as described by Jin-inchi et. al., Cancer Res. 50:6731–6737, 1990) was placed below the filter as a chemoattractant. Invasion assays were incubated for 16 hrs. at 37° C., after which cells remaining on the top of the filters were removed. Filters were then stained using the Diff-Quik™ staining set (Baxter, Miami, Fla.). Invasion was assessed as the number of cells which migrated through matrix material (Matrigel™), to the underside of the filters. For each filter, 10 fields were counted at 400×. All samples were run in duplicate. Controls consisted of cells treated with medium alone.

Figure 2:
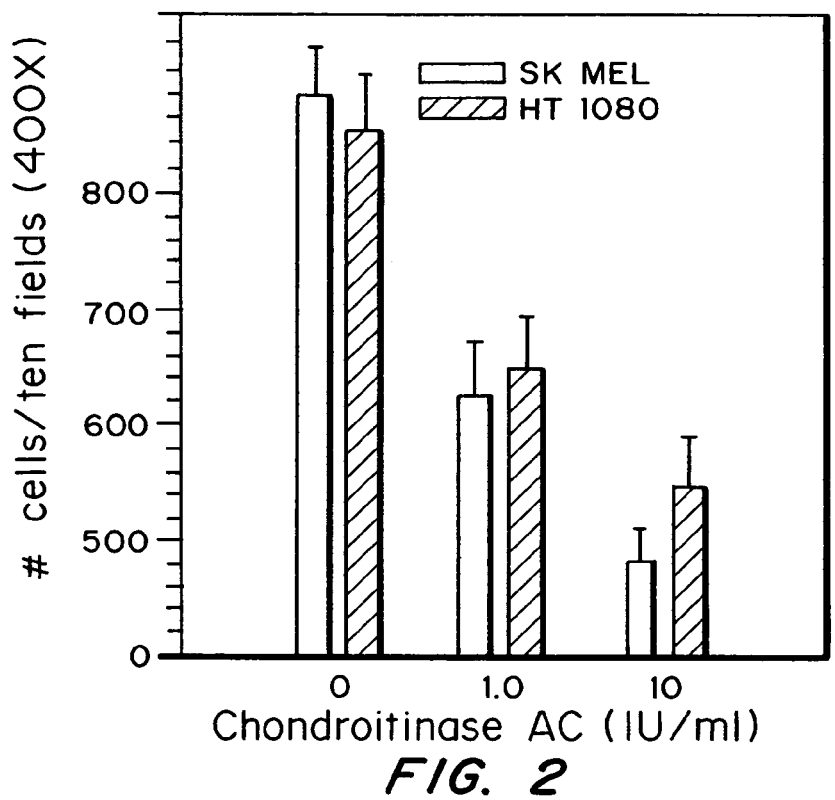
FIG. 2 is a graph of the dose-dependent effects (0, 1.0, and 10 IU/ml) of *Flavobacterium heparinum* derived Chondroitinase AC on the invasion of SK-MEL melanoma and HT-1080 fibrosarcoma cells into Matrigel™. Data are expressed as the number cells migrated through the filters and Matrigel™ and are the number of cells counted in ten 400× microscopic fields. Each bar represents the mean±sem of three experiments performed in duplicate.

Invasion of the melanoma cells (SK-MEL) was inhibited by 32% and 38% following treatment of cells with 1.0 and 10.0 IU/ml of chondroitinase AC, as shown in FIG. 2. Invasion of fibrosarcoma cells (HT-1080) was also inhibited by chondroitinase AC. Chondroitinase AC at concentrations of 1.0 and 10 IU/ml inhibited fibrosarcoma cell invasion by 27% and 40%, respectively, as shown in FIG. 2.

EXAMPLE 4

Effects on Tumor Cell Proliferation

Figure 3:
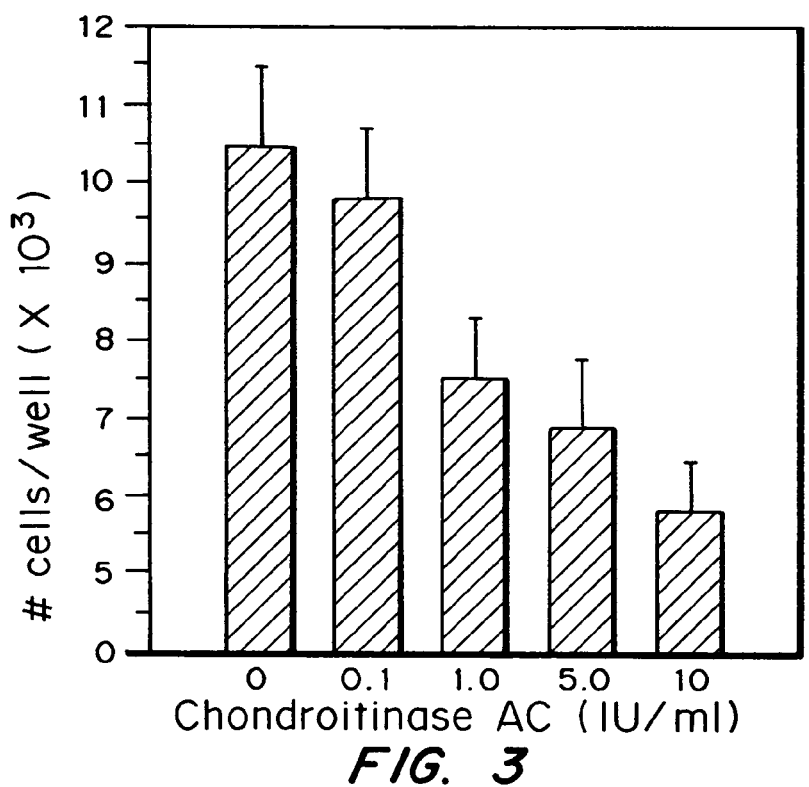
FIG. 3 is a graph of the dose-dependent effects of *Flavobacterium heparinum* derived Chondroitinase AC (ChAC) (0, 0.1, 1.0, 5.0, and 10 IU/ml) on melanoma cell proliferation in response to 10% serum. Data are the mean number of cells/well, 48 hrs after treatment of SK-MEL cells with either ChAC or medium alone (control). Each bar represents the mean±sem of four experiments performed in triplicate.

Human melanoma cells (SK-MEL) were obtained from the ATCC, Manassas, Va. Cells were cultured in MEM containing 1% antibiotics and 10% serum. The proliferation assay was performed as described by Denholm and Phan, Am J Pathol. 134(2):355–63 (1989). Briefly, cells were plated in MEM with 10% serum; 24 hrs later medium was replaced with serum free medium, and incubation continued for an additional 24 hrs. Cells were then treated with either serum free MEM alone, or MEM containing 0.1 to 10 IU/ml of chondroitinase AC for 1 hour at 37° C. Following enzyme treatment, cells were rinsed 1× with MEM, then given MEM with 10% serum and incubated for 48 hrs. Controls for each experiment were: (negative) untreated cells incubated in serum free medium, and (positive) untreated cells incubated in MEM with 10% serum. The number of cells per well was quantified using the CyQuant™ assay method from Molecular Probes, Eugene, Oreg. Fluorescence/well was determined using a CytoFluor™ Series 4000 fluorescent plate reader (PerSeptive Biosystems) and cell numbers calculated from a standard curve. Experiments were performed to determine if treatment of SK-MEL melanoma cells with chondroitinase AC would have an effect on proliferation of these cells. Melanoma cell proliferation in response to 10% serum was inhibited by 45% with 10 IU/ml of chondroitinase AC, as shown by FIG. 3.

EXAMPLE 5

Effects on Endothelial Cell Proliferation

Figure 4:
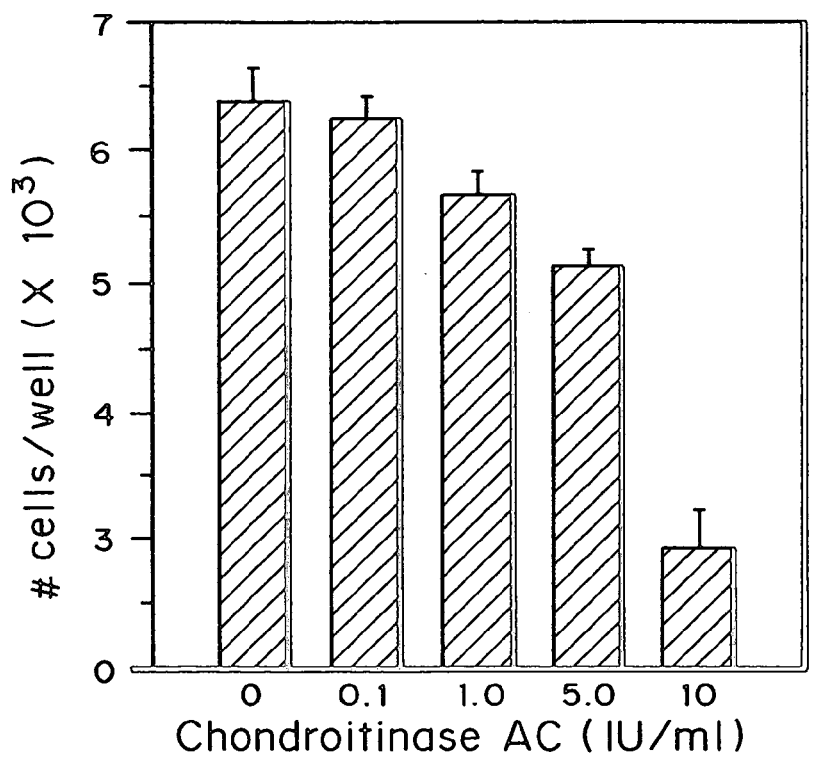
FIG. 4 is a graph of the dose-dependent effects of *Flavobacterium heparinum* derived Chondroitinase AC on the proliferation of endothelial cells in response to 20 ng/ml of vascular endothelial growth factor. Data are the mean±sem of five experiments performed in quadruplicate.

Endothelial cell proliferation assays were conducted essentially as those described in Example 4 for tumor cells, except that endothelial cells were plated at 1.5×10$^4$ cells/ml in MEM containing 10% serum. On Day 3 cells were treated with 0, 1 to 10 IU/ml of chondroitinase AC for 1 hr then rinsed with serum free medium and given fresh medium containing 20 ng/ml of VEGF. The number of cells/well was quantified 48 hrs later using the CyQuant™ assay as described in example 4. Chondroitinase AC treatment inhibited endothelial cell proliferation (FIG. 4) in a dose dependent manner. Endothelial cell proliferation was inhibited by 11 to 55% following treatment with 1.0 to 10 IU/ml of chondroitinase AC, respectively.

EXAMPLE 6

Effects on Angiogenesis

The effects of chondroitinase AC on angiogenesis were assessed in an in vitro system. Human endothelial cells (ATCC, Manassas, Va.) were grown in MEM with 10% serum. Cells were washed with PBS then treated with the indicated concentration of chondroitinase AC for 1 hr at 37 C. Following enzyme treatment, cells were washed, removed from dishes with trypsin, and resuspended in serum free medium to a concentration of 4×10$^5$ cells/ml. This endothelial cell suspension was mixed in a ratio of 1:1 with 2 mg/ml type I collagen (rat tail, Collaborative Biochemical Products), or in a ratio of 2:1 with 19 mg/ml growth factor-reduced Matrigel™. Ten ml of this cell suspension was added to the center of each well of a 48 well culture dish, and incubated for 30 mins at 37 C. Following formation, medium containing 2 mg/ml BSA and 20 ng/ml of VEGF (Peprotech, Rocky Hill, NJ) was added, with the indicated concentration of chondroitinase AC. Angiogenesis was assessed as the formation of Capillary-like Structures (CLS) after incubation for 3 days (collagen) or 6 days (Matrigel). To visualize and quantify the CLS, endothelial cells were labeled with 1 mM calcein AM (Molecular Probes Inc, Portland, Oreg.) for 30 mins. CLS were quantified by counting the number of CLS in 3, 100× fields.

Figure 5:
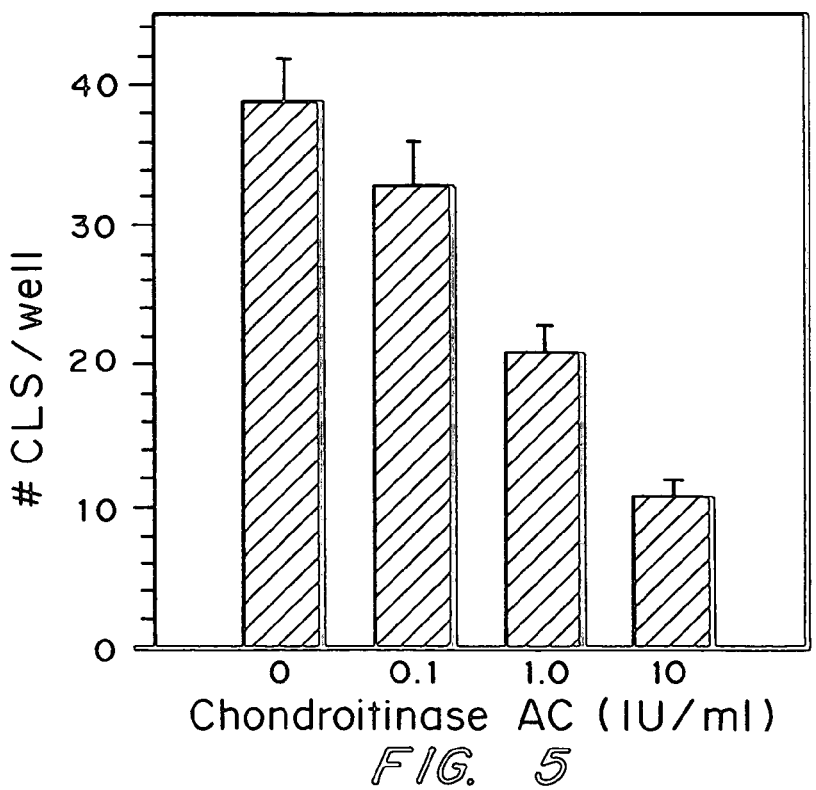
FIG. 5 is a graph of the dose-dependent effects of *Flavobacterium heparinum* derived Chondroitinase AC on angiogenesis within Matrigel™. Data are the number of capillary-like structures (CLS) present per 100× field. Each bar represents the mean±sem of five experiments performed in duplicate.

Chondroitinase AC inhibited angiogenesis in a dose-dependent manner. Angiogenesis was inhibited by 46 and 72% following treatment with 1.0 and 10 IU/ml of chondroitinase AC, respectively (FIG. 5).

EXAMPLE 7

Effects on Multiple Cellular Activities

The effects of chondroitinase AC, chondroitinase B and the combination of chondroitinase AC and B, on endothelial and tumor cell activities were compared. Melanoma or endothelial cells were treated with either medium alone (controls), 1.0 IU/ml or 5.0 IU/ml of one or both of the chondroitinase enzymes for one hour at 37° C. The cellular activities examined were tumor cell proliferation, tumor cell invasion, endothelial proliferation and angiogenesis, which were assayed as described in the previous examples.

Figure 6:
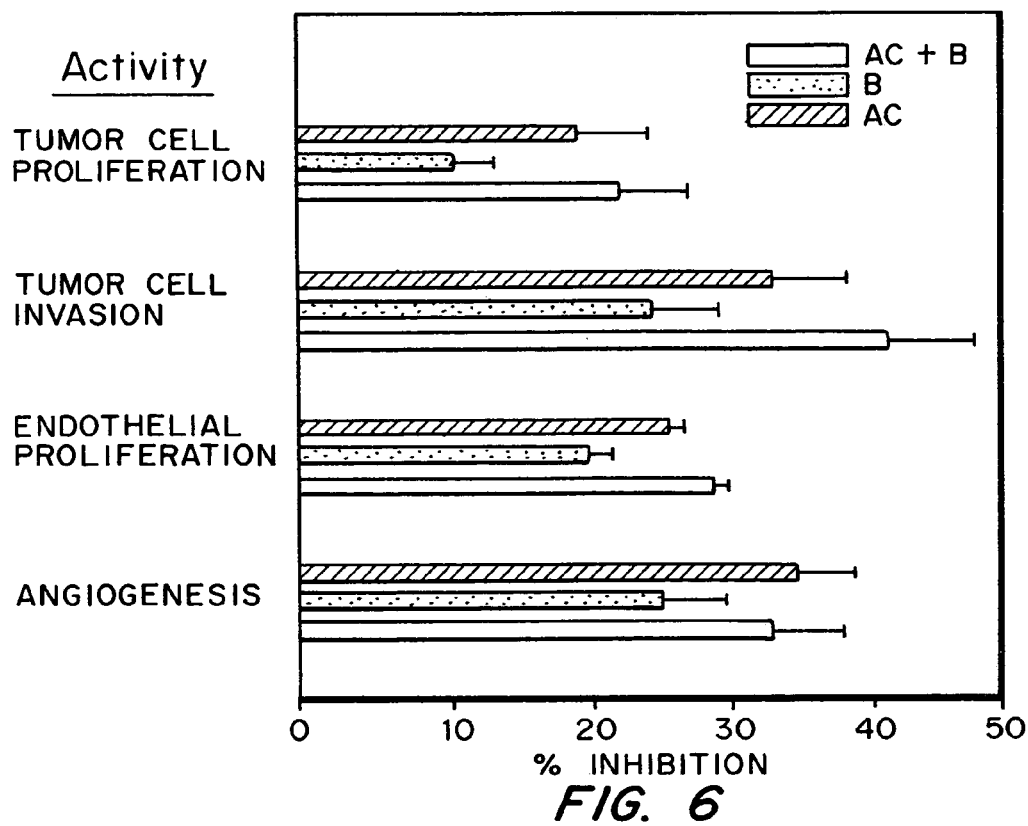
FIG. 6 is a graph of comparison of the effects of *Flavobacterium heparinum* derived Chondroitinase AC, and Chondroitinase B, and the combination of Chondroitinase AC and B on tumor cell proliferation, tumor cell invasion, endothelial proliferation and angiogenesis. The effects of 1.0 IU/ml or 5.0 IU/ml (endothelial proliferation) of Chondroitinase AC and Chondroitinase B, on these cellular activities were determined as described in FIGS. 2 through 5. Data are expressed as the % Inhibition, determined by comparing the responses of untreated and chondroitinase treated cells. Each bar represents the mean±sem of five experiments for each activity.
Figure 7:
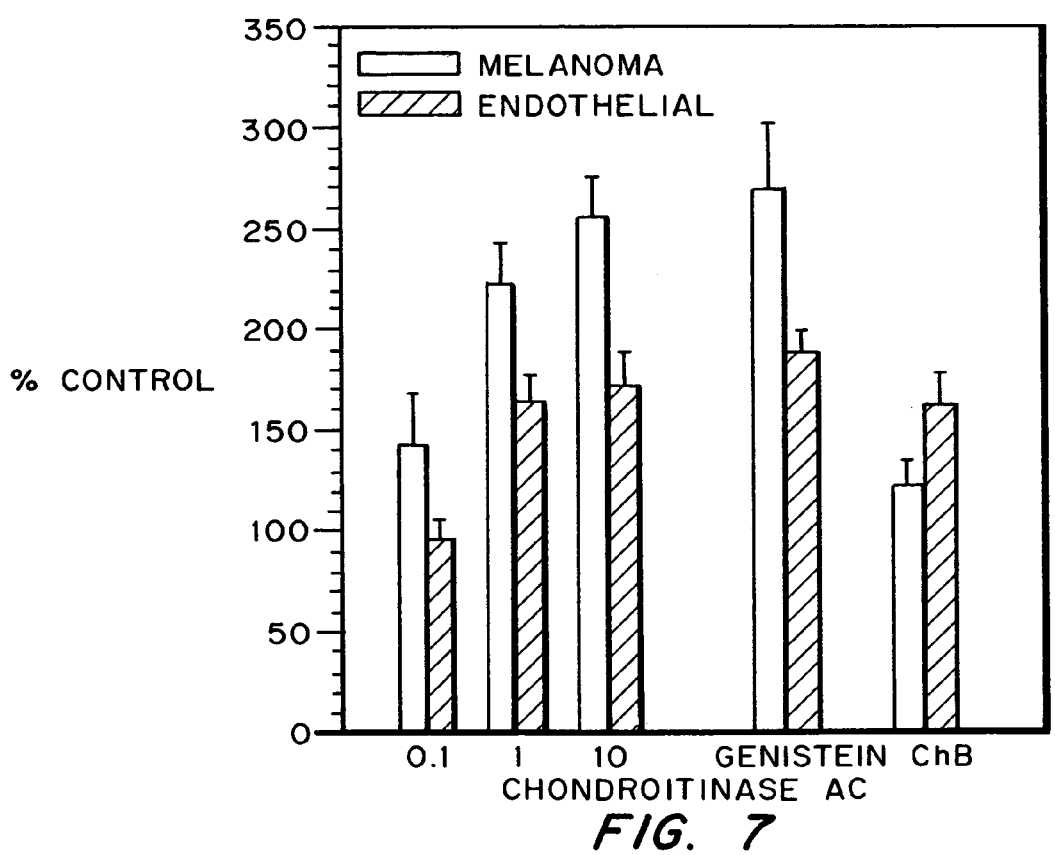
FIG. 7 is a graph of the effects of *Flavobacterium heparinum* derived Chondroitinase AC (0.1 to 10 IU/ml) and Chondroitinase B (1.0 IU/ml) on melanoma and endothelial cell apoptosis. Data are expressed as % control, determined by comparing the activity of chondroitinase treated cells with that of untreated controls (100%). The apoptosis-inducer, Genistein (40 mg/ml) was used as a positive control. Each bar represents the mean±sem of five experiments performed in duplicate.

Each enzyme had significant inhibitory effects on all the activities assayed, when compared to untreated controls as shown by FIG. 6. For each activity assayed, chondroitinase AC was more effective than chondroitinase B. However, this difference was significant only in regards to tumor cell proliferation. Further more, treating cells with chondroitinase AC alone was as effective in inhibiting cellular activities, as was a combination of chondroitinase AC and chondroitinase B, as shown by FIG. 7.

EXAMPLE 8

Effects on Apoptosis

The effects of Chondroitinase AC on tumor cell and endothelial cell apoptosis were assessed. This was done to determine if the induction of apoptosis by Chondroitinase AC might be the mechanism by which Chondroitinase AC inhibits the multiple cellular activities in Example 7.

Melanoma or endothelial cells were treated with either medium alone (negative controls), 0.10 IU/ml to 10.0 IS/ml of Chondroitinase AC, or 1.0 IU/ml of Chondroitinase B, 48 hrs at 37° C. As a positive control, cells were incubated in parallel, with 40 µg/ml of Genistein, a known inducer of apoptosis. At the end of the incubation period, cells were lysed and assayed for caspase-3 activity, as a marker of apoptosis. Caspase-3 assays were done using an assay kit from BioSource International.

Compared to untreated controls (100%) apoptosis was increased in both melanoma and endothelial cells (FIG. 7). Apoptosis (caspase-3 activity), was increased over that of controls by 64% in endothelial cells, and 150% in melanoma cells, following treatment with Chondroitinase AC. In comparison, Chondroitinase B did not significantly increase caspase-3 activity in melanoma cells, but did increase activity in endothelial cells 60% higher than that of controls. Genistein increased caspase activity of endothelial cells to 89% higher than controls, and of melanoma cells by 169% over controls.

EXAMPLE 9

Effects on Tumor Growth

The effects of Chondroitinase AC on tumor growth were assessed in mice. Mice (C57BL strain) weighed 20 to 25 g. Tumor cells were H-59, a sub-line of mouse Lewis lung carcinoma cells, as described by Brodt, Cancer Res. 46:2442–2448, 1986. Tumors were induced in mice, by the subcutaneous injection of 2×105 cells on day zero. Mice were palpitated daily for the appearance of tumors at the site of injection. Once tumors were palpable, mice were divided into two groups of 10 mice. Intra-tumor injections of either sterile saline (controls) or 55 IU of Chondroitinase AC (Treated) in saline, were done on Days 7,8,9, 11 and 13. Tumors were measured daily using calipers. In accordance with the animal protocol and regulations governing the use of animals in research, mice had to be sacrificed once tumor size reached 150 mm2. For this reason, mice in the control group were all terminated on Day 18.

Figure 8:
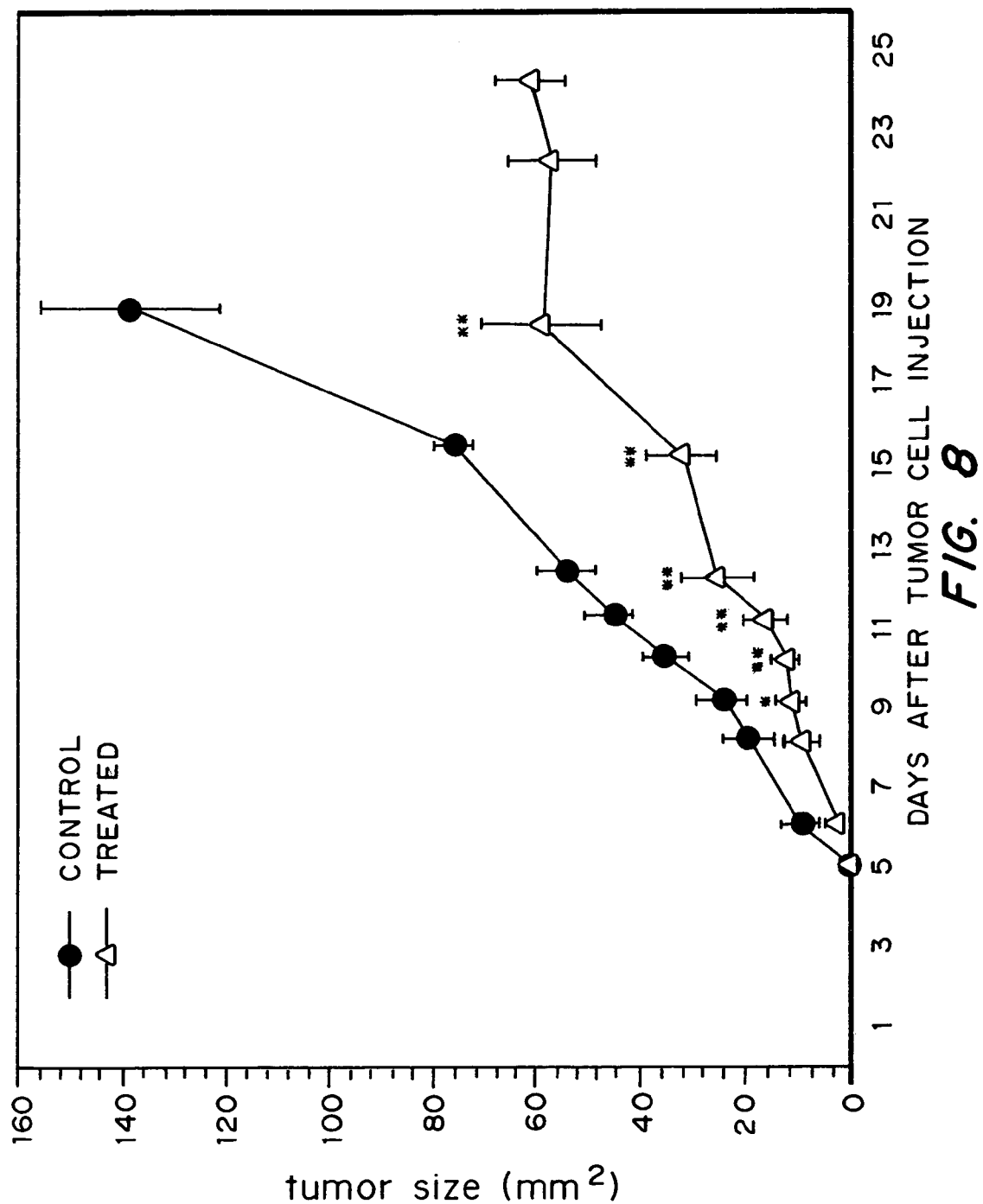
FIG. 8 is a graph of the effects of *Flavobacterium heparinum* derived Chondroitinase AC on tumor growth in vivo in mice. Mice were implanted subcutaneously with cells of a mouse Lewis lung carcinoma at Day 0. Animals were injected, directly into the tumor, on days 7, 8, 9, 11, and 13 with either 55 IU of chondroitinase AC or with a similar volume of saline. Animals were sacrificed and tumor size was measured on the indicated days. Data are shown as the tumor size in $mm^2$, and are the mean±sem of 10 mice per group. The asterisks indicate a statistical difference between groups; * indicates p=0.035, and **indicates<.005.

Tumor growth in mice treated with Chondroitinase AC was significantly reduced, when compared to saline-treated controls (FIG. 8). Comparison of the mean tumor size in the two groups, showed that tumors in Chondroitinase AC treated mice were smaller than those in the controls at all times. In addition, there was no further growth of the tumors in Chondroitinase AC-treated animals between Day 18 and 24, at which time the experiment was terminated.

Modifications and variations of the methods and compositions described herein are intended to be encompassed by the following claims. The teachings of the foregoing references cited herein are specifically incorporated by reference.

We claim:

1. A method to decrease angiogenesis comprising administering to a site in an individual in need of treatment thereof for an established disorder requiring angiogenesis an effective amount of a purified chondroitinase enzyme to decrease angiogenesis at the site, wherein the decrease in angiogenesis is measured as a decrease in endothelial cell proliferation or a decrease in the formation of capillary-like structures.

2. The method of claim 1 wherein the enzyme is selected from the group consisting of chondroitinase AC from *Flavobacterium heparinum*, chondroitinase B from *Flavobacterium heparinum*, a chrondroitin sulfate degrading enzyme from *Bacteroides* species, a chrondroitin sulfate degrading enzyme from *Proteus vulgaris*, a chrondroitin sulfate degrading enzyme from *Microcossus*, a chrondroitin sulfate degrading enzyme from *Vibrio* species, a chrondroitin sulfate degrading enzyme from *Arthrobacter aurescens*, and combinations thereof wherein these enzymes are expressed from recombinant nucleotide sequences in bacteria.

3. The method of claim 1 wherein the enzyme is a mammalian enzyme.

4. The method of claim 1 wherein the enzyme is a chrondroitinase AC.

5. The method of claim 1 wherein the chondroitinase is chondroitinase AC.

6. The method of claim 1 wherein the enzyme is administered to an individual having cancer as evidenced by palpable tumors.

7. The method of claim 6 wherein the cancer is a solid tumor and the enzyme is chondroitinase AC.

8. The method of claim 1 wherein the individual has a disorder in which angiogenesis is involved, the disorder being selected from the group consisting of rheumatoid arthritis: psoriasis; ocular angiogenic disease, rubeosis; Osler-Webber Syndrome; myocardial angiogenesis; plaque neovascularization; telangiectasia; hemophiliac joints; angiofibroma; Crohn's disease, atherosclerosis, scleroderma, hypertrophic scarring, adhesions, cirrhosis of the liver, pulmonary fibrosis following acute respiratory distress syndrom or other pulmonary fibrosis of the newborn, endometriosis, polyposis, obesity, uterine fibroids, prostatic hypertrophy, and amyloidosis.

9. The method of claim 1 wherein the enzyme is administered systemically.

10. The method of claim 1 wherein the enzyme is administered locally at or adjacent a site in need of treatment.

11. The method of claim 1 wherein the enzyme is administered in a controlled and/or sustained release formulation.

12. The method of claim 7 wherein the chondroitinase is administered in a dosage in the range of 0.1 to 250 IU chondroitinase AC/tumor for tumors in the size range from 20 $mm^3$ to 15 $cm^3$.

13. The method of claim 1 wherein the enzyme is administered in combination with another active agent selected from the group consisting of antibiotics, cytokine cytotoxic agents, and anti-inflammatories.

14. The method of claim 7 wherein the enzyme is administered after excision of the tumor.

15. The method of claim 9 wherein the enzyme is administered by a route selected from the group consisting of intravenous, intra-cranial, and depo.

16. The method of claim 9 wherein the enzyme is administered using an infusion pump.

17. The method of claim 1 wherein the enzyme is chondroitinase B.

18. The method of claim 8 wherein the enzyme is chondroitinase B.

19. The method of claim 1 wherein the individual has a disorder in which angiogenesis is involved, the disorder being selected from the group consisting of disease of excessive or abnormal stimulation of endothelial cells, diseases that have angiogenesis as a pathologic consequence, and scarring following transplantation.

20. The method of claim 1 wherein the enzyme is administered topically.

* * * * *